US00PP11996P2

(12) United States Plant Patent
Walden

(10) Patent No.: US PP11,996 P2
(45) Date of Patent: Jul. 17, 2001

(54) SHRUB ROSE PLANT NAMED 'JACSTAND'

(75) Inventor: John K. Walden, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/399,642

(22) Filed: Sep. 20, 1999

(51) Int. Cl.[7] ..... A01H 5/00
(52) U.S. Cl. ..... Plt./102
(58) Field of Search ..... Plt./102, 130, 132

(56) References Cited

U.S. PATENT DOCUMENTS

P.P. 7,319 * 9/1990 McGredy ..... Plt./102
P.P. 10,070 * 10/1997 Carruth ..... Plt./102

* cited by examiner

*Primary Examiner*—Howard J. Locker
(74) *Attorney, Agent, or Firm*—Klarquist Sparkman Campbell Leigh & Whinston, LLP

(57) ABSTRACT

A shrub rose plant having red and white striped flowers; clustering bloom habit; dark green, glossy foliage; and very good disease resistance.

1 Drawing Sheet

The present invention relates to a new and distinct variety of rose plant of the shrub class which was originated by me by crossing an unnamed seedling with the variety JACliang (U.S. Plant Pat. No. 8,402).

The primary objective of this breeding was to produce a new rose variety having the striped flower, dark green, glossy foliage and clustering bloom habit of the seed parent, and the larger, 1½ to 2 inch flower, higher petal count and health of the pollen parent. The objective was substantially achieved, along with other desirable improvements, as evidenced by the following unique combination of characteristics that are outstanding in the new variety and that distinguish it from its parents, as well as from all other varieties of which I am aware:

1. Bright red and white (aging to red and pink) striped flower;
2. Dark green, glossy foliage;
3. Medium to large flower clusters;
4. Petal count of 20–25 petals;
5. 1½ inch to 2 inch fully open bloom;
6. Very good disease resistance and vigor.

Asexual reproduction of this new variety by cuttings, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) colour chart, except where ordinary dictionary significance of color is indicated.

Parentage:

*Seed parent.*—Unnamed seedling (MACminmo — U.S. Plant Pat. No. 7,319×MORpapplay — U.S. Plant Pat. No. 6,548).

*Pollen parent.*—JACliang (U.S. Plant Pat. No. 8,402).

Classification:

*Botanical.*—*Rosa hybrida.*

*Commercial.*—Shrub rose.

FLOWER

Observations made from specimens grown in a garden environment at Somis, Calif. in Aug. 1999.

Blooming habit: Recurrent.

Bud:

*Size.*—About ⅝ to ¾ inch long when the petals start to unfurl.

*Form.*—The bud form is pointed ovoid.

*Color.*—When sepals first divide, bud color is variable, but predominantly Red Group 46A, with stripes of new White Group 155C. When half blown, the upper and lower sides of the petals are near Red Group 46D, with white stripes of near White Group 155C and flecks of Red Group 46A and with a ¼ inch crescent of Yellow Group 6C at the petal base.

*Sepals.*—Color: Near Yellow-Green Group 146B, with an overlay of Greyed-Purple Group 183A. Surface texture: Slight roughness; glandular. These are three lightly appendaged sepals. There are two unappendated sepals with hairy edges.

*Receptacle.*—Color: Yellow-Green Group 146B. Shape: Pear. Size: Small (about ¼ inch×¼ inch). Surface: Hairy.

*Peduncle.*—Length: Short (about 1 inch). Surface: Smooth. Color: Yellow-Green Group 146B. Where exposed to bright sunlight the color is Greyed-Purple Group 183B. Strength: Erect.

Bloom:

*Size.*—Small. Average open size is 1¾ inches.

*Borne.*—In flat clusters of 9 to 15 blooms.

*Stems.*—Strength: Normal. Average length is about nine inches.

*Form.*—When first open: Cupped. Permanence: Flattens.

*Petalage.*—Number of petals under normal conditions: 20–25.

*Color.*—The upper sides of the petals are Red Group 46B with irregular strips of White Group 155C, with fleckes of Red Group 46B. The reverse sides of the petals are near Red Group 53D with irregular stripes of White Group 155C. The base of each petals has a ⅛ inch to ¼ inch Yellow Group 5C crescent. The major color on the upper side is Red Group 46B, with stripes initially of White Group 155C, but which as the bloom ages, acquire a pinkish hue of near Red Group 48C.

*Variegations.*—Striping as described above is variable; flowers can be nearly all Red Group 46B to nearly all White Group 155C with flecks of Red Group 46B.

*Discoloration.*—The general tonality at the end of the first day: Red Group 46B and White Group 155C. At the end of the third day: Unchanged. With further aging, color becomes Red Group 53C with stripes of Red Group 54B.

*Fragrance.*—None.

Petals:

*Texture.*—Leathery.

*Shape.*—Oval and slightly pointed.

*Form.*—Flat to tips slightly recurved.

*Arrangement.*—Imbricated (shingle-like). Petaloids in the center are few (three to five).

*Persistence.*—Petals drop off cleanly before drying.

*Lastingness.*—On the plant: Long (about 9 to 11 days). As a cut flower: Not tested.

*Reproductive parts:*

*Anthers.*—Size: Medium (⅛ inch×1/16 inch). Quantity: Many. Color: Between Yellow-Orange Group 16C and Yellow-Orange Group 16D. Arrangement: Regular around styles.

*Filaments.*—Color: Between Yellow-Orange Group 16C and Yellow-Orange Group 16D.

*Pollen.*—Color: Yellow-Orange Group 22A.

*Styles.*—Color: Yellow-Green Group 145C.

*Stigmas.*—Color: Between Greyed-Yellow Group 162C and Greyed-Yellow Group 162D.

Plant:

*Form.*—Shrub.

*Growth.*—Vigorous; upright and arching slightly. At maturity, height is 3½ to 4 feet, width is 3 to 3½ feet. Plant is hardy in U.S.D.A. zones 5–11. In colder zones, the plant requires winter protection.

Foliage: Number of leaflets on normal mid-stem leaves: Seven.

*Size.*—About 3⅛ inches long×1½ inches wide.

*Quantity.*—Normal.

*Color.*—New foliage: Upper and lower surfaces: Greyed-Red Group 178A. Old foliage: Upper surface: Between Green Group 137A and Green Group 137B. Lower surface: Between Yellow-Green Group 147B and Yellow-Green Group 147C.

Leaflets:

*Shape.*—Elliptic.

*Texture.*—Leathery; glossy.

*Edge.*—Serrated.

*Serration.*—Double.

*Petiole rachis.*—Color: Near Greyed-Red Group 178A.

*Petiole underside.*—Usually with prickles; near Yellow-Green Group 152B.

*Stipules.*—Medium (about ⅝ inch), serrated.

*Disease resistance.*—Resistant to mildew, blackspot and rust under normal growing conditions.

Wood:

*New wood.*—Color: Yellow-Green Group 146D. Bark: Smooth.

*Old wood.*—Color: Yellow-Green Group 146B. Bark: Smooth.

Prickles:

*Quantity.*—On main canes from base: Ordinary. On laterals from main canes: Ordinary.

*Form.*—Medium (5/16 inch to ⅜ inch).

*Color when young.*—Near Greyed-Red Group 178A.

*Color when mature.*—Between Greyed-Orange Group 165B and Greyed-Orange Group 165C.

Small prickles:

*Quantity.*—On main stalks: None. On laterals: None.

I claim:

1. A new and distinct variety of rose plant of the shrub class, substantially as herein shown and described, characterized particularly by its red and white striped flowers; clustering bloom habit; dark green, glossy foliage; and very good disease resistance.

* * * * *

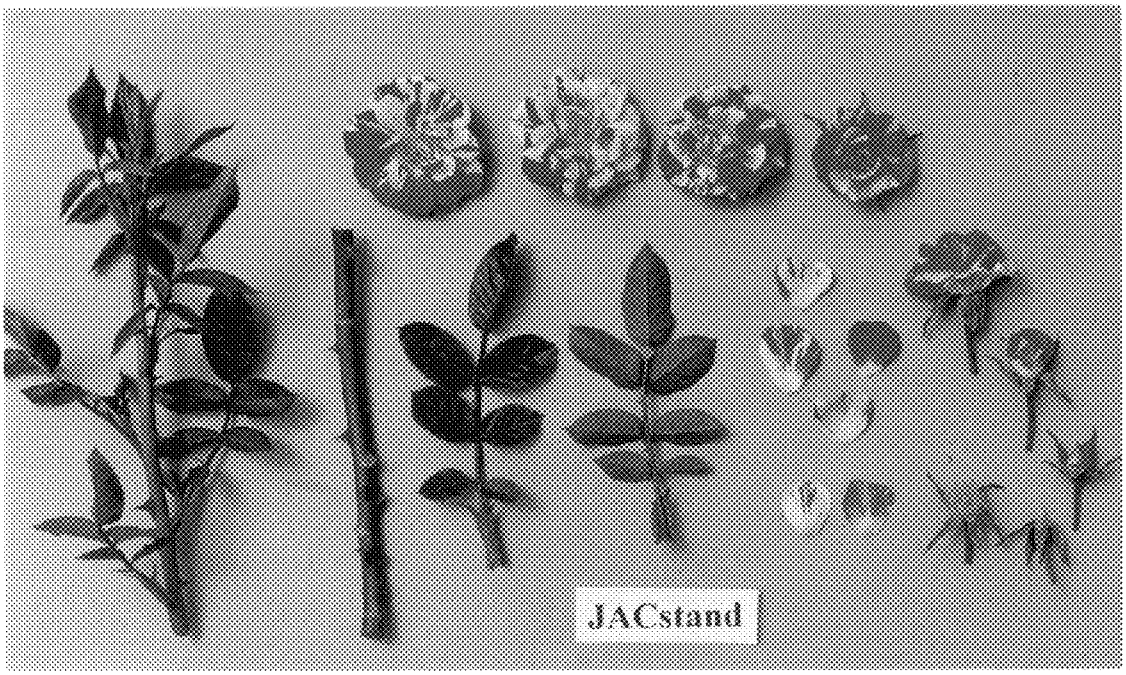
JACstand